United States Patent [19]
Sorkin, Jr.

[11] Patent Number: 5,952,393
[45] Date of Patent: Sep. 14, 1999

[54] COMPOSITION FOR REDUCING SERUM CHOLESTEROL LEVELS

[76] Inventor: Harlan Lee Sorkin, Jr., 2616 Stillwater Dr., Champaign, Ill. 61821

[21] Appl. No.: 09/022,807

[22] Filed: Feb. 12, 1998

[51] Int. Cl.⁶ .................................................. A61K 31/045
[52] U.S. Cl. ........................... 514/729; 514/724; 514/739
[58] Field of Search ..................................... 514/729, 724, 514/739

[56] References Cited

U.S. PATENT DOCUMENTS

| | | | |
|---|---|---|---|
| 4,391,732 | 7/1983 | Lundmark | 252/356 |
| 5,502,045 | 3/1996 | Miettinen et al. | 514/182 |
| 5,663,156 | 9/1997 | Granja et al. | 514/164 |
| 5,770,749 | 6/1998 | Kutney et al. | 552/545 |

OTHER PUBLICATIONS

Snider S.R., "Octacosanol in parkinsonism [letter]" Ann Neurol Dec. 1984; 16(6): 723.

Arruzazabala, M.L. et al. "Effect of policosanol on cerebral ishemia in Mongolian gerbils: role of prostacyclin and thromboxane A2" Prostaglandin Leukot Essent Fatty Acids Sep. 1993;49(3):695–7.

Arruzazabala, M.L., et al. "Effects of policosanol on platelet aggregation in rats" Thromb Res Feb. 1, 1993;69(3):321–7.

Kabir, Y., et al. "Biodistribution and metabolism of orally administered octacosanol in rats" Ann Nutr Metab 1993;37(1):33–8.

Menendez, R. et al. "Cholesterol–lowering effect of policosanol on rabbits with hypercholesterolaemia induced by a wheat starch–casein diet" Br J Nutri Jun. 1997;77(6):923–32.

Arrazazabala M.L., et al. "Effect of policosanol successive dose increases on platelet aggregation in healthy volunteers" Pharmacol Res Nov.–Dec. 1996;34(5–6):181–5.

Valdes, S. et al. "Effect of policosanol on platelet aggregation in healthy volunteers" Int J Clin Pharmacol Res 1996;16(2–3):67–72.

Canetti, M. et al. "A two–year study on the efficacy and tolerability of policosanol in patients with type II hyperlipoproteinaemia" Int J Clin Pharmacol Res 1995; 15 (4):159–65.

Arruzazabala, M.L. et al. "Cholesterol–lowering effects of policosanol in rabbits" Biol Res 1994;27(3–4):205–8.

Menendez, R. et al. "Policosanol inhibits cholesterol biosynthesis and enhances low density lipoprotein processing in cultured human fibroblasts" Biol Res 1994;27(3–4):199–203.

Batista, J. et al. "Effect of policosanol on hyperlipidemia and coronary heart disease in middle–aged patients. A 14–month pilot study" Int J Clin Pharmacol Ther Mar. 1996;34(3):134–7.

Torres, O. et al. "Treatment of hypercholesterolemia in NIDDM with policosanol" Diabetes Care Mar. 1996;18(3):393–7.

Noa, M. "Effect of policosanol on isoprenaline–induced myocardial necrosis in rats" J Pharm Pharmacol Apr. 1994; 46(4):282–5.

Rodriguez–Echenique, C. et al. "Effects of policosanol chronically administered in male monkeys (*Macaca arctoides*)" Food Chem Toxicol Jun. 1994;32(6):565–75.

Aleman, C.L. et al. "A 12–month study of policosanol oral toxicity in Sprague Dawley rats" Toxicol Lett 1994 Jan. 1994;70(1):77–87.

Kato, S. et al. "Octacosanol affects lipid metabolism in rats fed on a high–fat diet." British Journal of Nutrition. v. 73, Mar. 1995, pp. 433–441.

Aleman, C.L. et al. "Carcinogenicity of policosanol in mice: an 18–month study." Food Chem Toxicol Jul. 1995 ;33(7):573–8.

*Primary Examiner*—Raymond Henley, III
*Attorney, Agent, or Firm*—Cummings & Lockwood

[57] ABSTRACT

A composition for reducing serum cholesterol in humans and animals is provided. The composition includes phytosterol and policosanol which together produce a synergistic effect in lowering serum cholesterol levels. Preferably the composition includes about 3.2:1 parts by weight of phytosterol and policosanol.

10 Claims, No Drawings

COMPOSITION FOR REDUCING SERUM CHOLESTEROL LEVELS

FIELD OF THE INVENTION

The present invention relates generally to compositions for reducing serum cholesterol levels and, more particularly, to a composition for lowering serum cholesterol including policosanols and phytosterols.

BACKGROUND OF THE INVENTION

Elevated serum cholesterol levels (>200mg/dL) have been indicated as a major risk factor for heart disease, the leading cause of death among Americans. As a result, experts have recommended that those individuals at high risk decrease serum cholesterol levels through dietary changes, a program of physical exercise, and lifestyle changes. It is recommended that the intake of saturated fat and dietary cholesterol be strictly limited and that soluble fiber consumption be increased. Strictly limiting the intake of saturated fat and cholesterol does not, itself, present a risk to proper health and nutrition. Even where saturated fat and cholesterol are severely restricted from the diet, the liver remains able to synthesize sufficient quantities of cholesterol to perform necessary bodily functions.

More recently, experts have begun to examine the individual components of the lipid profile, in addition to the total cholesterol level (TC). While an elevated TC is a risk factor, the levels of the various forms of cholesterol which make up TC may also be risk factors. Elevated low-density lipoprotein (LDL) is a cause for concern, as these loosely packed lipoproteins are more likely to lodge within the cardiovascular system leading to the formation of plaque. Low levels of high-density lipoproteins (HDL) are an additional risk factor, as they serve to sweep artery clogging cholesterol from the blood stream. A better indication of risk appears to be the ratio of TC:HDL.

A number of nutritional factors have been shown to improve serum cholesterol levels. For example, the use of phytosterols has been well documented in human clinical trials and in animal studies to lower serum cholesterol levels. This cholesterol lowering effect has been attributed to interference with the absorption of dietary cholesterol. Phytosterols, being structurally similar to cholesterol, competitively bind with cholesterol sterol receptor sites, thus preventing cholesterol uptake. Unlike their cholesterol counterparts, phytosterols are very poorly absorbed, and some are not absorbed at all. Therefore, phytosterols do not contribute to an increase in serum cholesterol levels. In addition to competing for receptor sites, phytosterols also compete for the enzyme cholesterol esterase. This enzyme is required by cholesterol for its breakdown to components which may be absorbed through the microvilli which line the wall of the small intestine. Thus, phytosterols also impede the enzymatic breakdown and intestinal absorption of cholesterol, which further reduces serum cholesterol levels.

Plant derived long-chained aliphatic alcohols have also been documented to reduce serum cholesterol levels in experimental models, healthy humans and in type II hypercholesterolemic patients. These aliphatic alcohols, collectively known as policosanol, have been employed in the treatment of elevated serum cholesterol levels in only the past five years, but policosanol has shown much promise, as reported in a number of published human clinical trials. The mechanism of action has not yet been elucidated, but policosanol's effectiveness is attributed to its influence on the bio-synthesis of cholesterol within the liver. This accounts for the ability of policosanol to not only decrease total cholesterol, but also to decrease LDL serum levels and increase HDL levels.

SUMMARY OF THE INVENTION

The present invention provides a composition for reducing serum cholesterol levels in humans and animals. The composition comprises from about 5% to about 75% by weight of phytosterol, and from about 1% to about 60% by weight of policosanol. The composition further comprises from 0% to about 65% by weight of pharmaceutically acceptable formulation aids, such as diluents, stabilizers, binders, buffers, lubricants, coating agents, preservatives, emulsifiers and suspension agents.

In a preferred embodiment, the composition comprises from about 10% to about 60% by weight of phytosterol, and from about 3% to about 46% by weight of policosanol. In the most preferred embodiment of the invention, the composition comprises about 3.2:1 parts by weight of phytosterol and policosanol.

DETAILED DESCRIPTION OF THE INVENTION

As noted previously, policosanol is a mixture of high-molecular weight aliphatic alcohols. These alcohols occur naturally in wax form and are characterized by fatty alcohol chains ranging from 20 to 39 carbon atoms in length. The major component of policosanol are the aliphatic alcohols octacosanol and triacontanol. Policosanol is isolated from a number of different plant sources, including sugar cane wax and rice bran wax. The policosanol used in the preferred embodiment of the invention is obtained from rice bran wax and has the formulation set forth below in Table I. This material is sold under the name "Rice Bran Wax" and is available from Traco Labs, Inc. It should be understood, however, that the invention is not limited in this regard and that policosanol commonly available from other naturally occurring sources may be utilized.

TABLE I

Rice Bran Wax typical long-chain aliphatic alcohol profile:

| Carbon | Fatty Alcohol | Composition (%) |
|---|---|---|
| $C_{22}OH$ | Docosanol (Behenyl Alcohol) | 0.36 |
| $C_{24}OH$ | Tetracosanol (Lignoceryl Alcohol) | 3.21 |
| $C_{26}OH$ | Hexacosanol (Cerotyl Alcohol) | 2.93 |
| $C_{28}OH$ | Octacosanol (Montanyl Alcohol) | 5.59 |
| $C_{30}OH$ | Triacontanol (Melissyl Alcohol) | 8.35 |
| $C_{32}OH$ | Dotriacontanol | 4.64 |
| $C_{34}OH$ | Tetratriacontanol | 2.22 |
| $C_{36}OH$ | Hexatriacontanol | .50 |
| | Total policosanols | 23–33% |

Phytosterols are also mixtures of long-chained aliphatic alcohols in a wax form. They are naturally occurring in many common vegetable food products. The particular phytosterol used in the preferred embodiment of the invention is derived from vegetable oil and has the formulation set forth in Table 2. This material is sold under the trademark "CHOLESTATIN" and is available from Traco Labs, Inc. Again, however, it should be understood that the invention is not limited to this particular phytosterol product, and that any number of other commonly available phytosterols can be used.

TABLE II

| Phytosterol composition: | |
|---|---|
| Total sterols Assay | 88% Min. Specification |
| B-Sitosterol | 43% Min. |
| campesterol | 25% Min. |
| stigmasterol | 15% Min. |

As noted previously, phytosterol and policosanol lower serum cholesterol links by two independent and unrelated mechanisms of action. However, both compounds together are expected to have a synergistic effect on lowering serum cholesterol. As previously mentioned, phytosterols impede the enzymatic breakdown and intestinal absorption of cholesterol, which reduces serum cholesterol levels. Policosanol acts directly on the cholesterol synthesis pathway itself, thereby inhibiting the bio-synthesis of cholesterol from saturated fat. However, both compounds together are expected to have a synergistic effect on lowering serum cholesterol levels. Thus, the combination of both phytosterol and policosanol into a single composition is expected to provide a more effective treatment for elevated serum cholesterol than would be expected from the additive effect of both components.

Examples of compositions made according to the invention is set forth below:

EXAMPLE 1
Tablet Formula:

| ingredient | amt/cap | function |
|---|---|---|
| "CHOLESTATIN" (Min. 88% phytosterols) | 250 mg | active |
| "Rice Bran Wax" (23–33% policosanols) | 250 mg | active |
| Calcium phosphate | 261.7 mg | base |
| Cellulose | 49.4 mg | tablet coating agent |
| Stearic acid | 23.8 mg | lubricant |
| Magnesium stearate | 6.8 mg | lubricant |
| Silicon dioxide | 9.4 mg | diluent |

EXAMPLE 2
Soft Gelatin Capsule Formulation:

| ingredient | amt/cap | function |
|---|---|---|
| "CHOLESTATIN" (Min. 88% phytosterols) | 250 mg | active |
| "Rice Bran Wax" (23–33% policosanols) | 250 mg | active |
| Medium Chain Triglycerides | 700 mg | diluent/ emulssifying suspending agent |

Previous clinical and toxicological testing of policosanol and phytosterol has shown that the tolerance of both components is good. Significantly larger doses of both waxes are readily tolerated. Occasional GI irritation might be expected at extremely high doses, far greater than the normal dosage range. In the event such irritation should occur, it would be expected to be minimal, and would not pose any risk to health.

Toxicology performed on the 50% phytosterol/50% rice bran wax composition has proven that the composition is non-toxic at an oral dose of 5000 mg/kg of body weight in Sprague-Dawley rats. Accordingly, oral dosages in humans of up to a maximum dosage of 1500 mg administered three times per day is considered appropriate.

While preferred embodiments have been shown and described, various modifications and substitutions may be made without departing from the spirit and scope of the invention. Accordingly, it is to be understood that the present invention has been described by way of example and not by limitation.

We claim:

1. A composition for reducing serum cholesterol levels in humans and animals, said composition comprising: from about 5% to about 75% by weight of phytosterol, from about 1% to about 60% by weight of policosanol, said policosinal including a mixture of high molecular weight alyphatic alcohols which occur naturally in wax form and which are derived directly from plants, and from 0% to about 65% by weight of pharmaceutically acceptable formulation aids.

2. The composition of claim 1, wherein the mixture comprises from about 10% to about 60% by weight of phytosterol, and from about 3% to about 46% of by weight of policosanol.

3. The composition of claim 1, wherein the composition comprises about 3.2:1 parts by weight of phytosterol and policosanol.

4. The composition of claim 1, wherein the formulation aids comprise diluents, stabilizers, binders, buffers, lubricants, coating agents, preservatives, emulsifiers and suspension agents.

5. The composition of claim 1, wherein the policosanol is derived from rice bran wax.

6. The composition of claim 1, wherein the phytosterol is derived from vegetable oil.

7. A composition for reducing serum cholesterol levels in humans and animals, said composition comprising: from about 10% to about 60% by weight of phytosterol derived from vegetable oil, from about 3% to about 46% by weight of policosanol derived from rice bran wax, said policosinol including a mixture of high molecular weight aliphatic alcohols which occur naturally in wax form and which are derived directly from plants, and from 0% to about 65% by weight of pharmaceutically acceptable formulation aids.

8. The composition of claim 7, wherein the composition comprises about 3.2:1 parts by weight of phytosterol and the policosanol.

9. The composition of claim 8, wherein the composition comprises 220 mg of phytosterol and 69.5 mg of policosanol.

10. The composition of claim 9, wherein the composition is incorporated into a tablet or capsule formulation further comprising diluents, stabilizers, binders, buffers, lubricants, coating agents, preservatives, emulsifiers and suspension agents.

* * * * *